United States Patent
Knecht

(10) Patent No.: US 9,632,015 B2
(45) Date of Patent: Apr. 25, 2017

(54) HYDROSTATIC HEAD TESTER ARRANGEMENT

(71) Applicant: TEXTEST AG, Schwerzenbach (CH)

(72) Inventor: Hugo Knecht, Schöfflisdorf ZH (CH)

(73) Assignee: TEXTEST AG, Schwerzenbach (CH)

( * ) Notice: Subject to any disclaimer, the term of this patent is extended or adjusted under 35 U.S.C. 154(b) by 82 days.

(21) Appl. No.: 14/433,571

(22) PCT Filed: Oct. 15, 2012

(86) PCT No.: PCT/EP2012/070427
§ 371 (c)(1),
(2) Date: Apr. 3, 2015

(87) PCT Pub. No.: WO2014/060015
PCT Pub. Date: Apr. 24, 2014

(65) Prior Publication Data
US 2015/0226655 A1   Aug. 13, 2015

(51) Int. Cl.
*G01N 3/12* (2006.01)
*G01N 15/08* (2006.01)

(52) U.S. Cl.
CPC ........... *G01N 3/12* (2013.01); *G01N 15/0806* (2013.01); *G01N 15/0826* (2013.01)

(58) Field of Classification Search
CPC .. G01N 15/0826; G01N 3/12; G01N 15/0806; G01N 15/08; G01N 15/082
USPC ............ 73/38, 37, 49.5, 49.8, 818, 826, 866
See application file for complete search history.

(56) References Cited

U.S. PATENT DOCUMENTS

| 2,658,386 | A | * | 11/1953 | Guichard | G01N 3/12 73/37 |
| 3,248,930 | A | | 5/1966 | Speegle et al. | |
| 3,534,587 | A | * | 10/1970 | Grenci | F16J 13/00 73/49.8 |
| 5,474,633 | A | * | 12/1995 | Myers | B41F 16/00 156/230 |
| 5,535,616 | A | * | 7/1996 | Bors | G01N 1/34 73/38 |
| 7,475,591 | B2 | * | 1/2009 | Buckley | G01M 3/2823 73/37 |
| 2011/0296901 | A1 | * | 12/2011 | Nichols | G01M 3/28 73/49.8 |

OTHER PUBLICATIONS

Automatic Hydrostatic Head Tester FX 3000 Hydrotester III, Aug. 2004, http://www.2456.com/physhows/Libero e.pdf.
Textest, Nonwovens Industry, Aug. 2004.
Partial International Search for PCT/EP2012/070427 filed on Oct. 15, 2012.

* cited by examiner

*Primary Examiner* — Hezron E Williams
*Assistant Examiner* — Marrit Eyassu
(74) *Attorney, Agent, or Firm* — Notaro, Michalos & Zaccaria P.C.

(57) ABSTRACT

A hydrostatic head tester arrangement has a frame, a test pressure generating device, a clamping device having first clamping ring and a second clamping ring and wherein a power gain element is connected to the first clamping ring. Further, the power gain element is connected to an actuation lever via a resilient member.

12 Claims, 6 Drawing Sheets

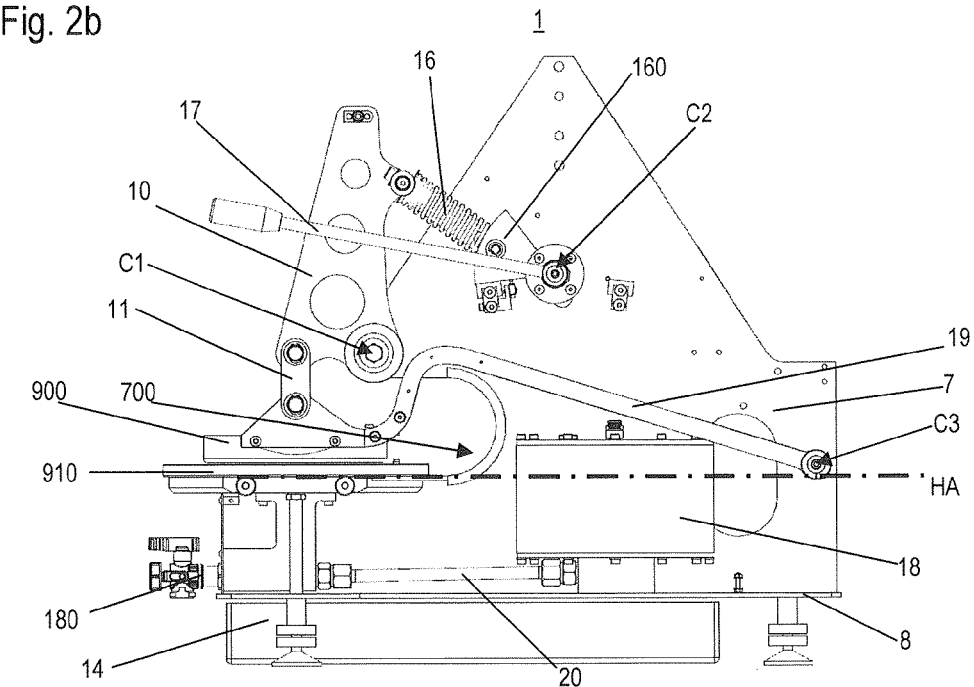

HYDROSTATIC HEAD TESTER ARRANGEMENT

Figure 1:
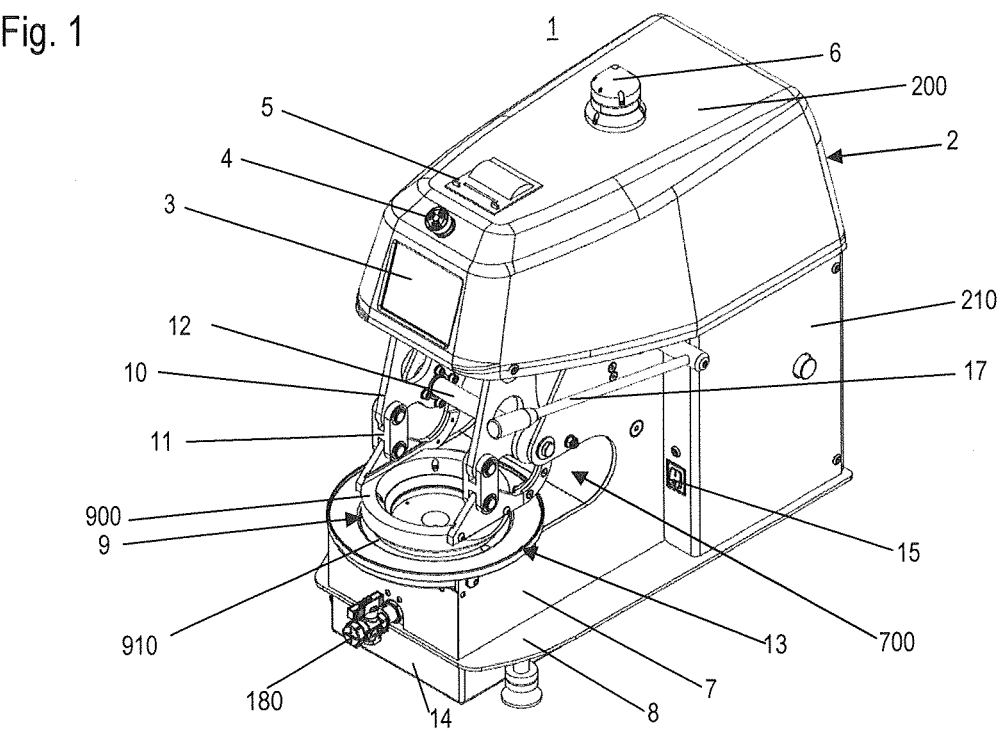

The present invention relates to a hydrostatic head tester arrangement according to the preamble of claim 1. Another aspect of the invention relates to a method for determining the resistance of a test specimen to liquid penetration in operating a hydrostatic head tester arrangement according to the present invention.

It is known to utilize hydrostatic head tester arrangements for determination of the resistance of test specimens to water penetration. The test specimens can be e.g. plastic foils, coated and uncoated fabrics, non-wovens.

An object of the present invention is to provide an improved hydrostatic head tester arrangement which can be operated safely.

The object is solved by the features given in the characterizing part of claim 1. Further embodiments of the invention are given in dependant claims.

A hydrostatic head tester arrangement according to the present invention comprises a frame, a test pressure generating device, a clamping device having a first clamping ring and a second clamping ring. A power gain element is connected to the first clamping ring. Further, the power gain element is connected to an actuation lever via a resilient member. In addition, a power transmission device is provided comprising a movable steering rod, its operating free end arranged distant from the power gain element in its inactivated state and engaging the power gain element in its activated state. This allows operating the arrangement safely in firstly, actuating the lever manually to fixate in place a test specimen with the aid of the clamping device and secondly, after the clamping device is brought into a designated closed position, the power transmission force device is actuated in order to ensure that the test specimen is maintained in its position when a test pressure is exerted on one surface of the test specimen. It is conceivable to implement the test pressure generating device as a test pressure generating container or as a test pressure generating device having a water column or as a pressure impinged water conduit.

It is conceivable to implement the power gain element comprising two cheeks arranged in parallel manner to each other.

Thereby, the hydrostatic head tester arrangement can safely be operated since the arrangement allows positioning of a test specimen safely into its designated position, i.e. without the risk to bruise a finger of the user.

In one embodiment, the first clamping ring is an upper clamping ring and the second clamping ring is a lower clamping ring, wherein a guide arm is attached to the upper clamping ring and is pivotally connected to the frame and the power gain element is connected to the upper clamping ring or to the guide arm via an articulation member.

In one embodiment, the pressure force actuation member comprises a pneumatic pressure cylinder or a hydraulic pressure cylinder or an electric driven pressure spindle.

In one embodiment, the power transmission device is coupled electrically or pneumatically or hydraulically to an actuation device to be activated.

Thereby, the power transmission device is only activated when the test specimen is clamped in its designated clamping position between the upper clamping ring and the lower clamping ring, i.e. the clamping device is in its defined closed position. Thus, the risk to bruise a finger of the user due to premature activation of the power transmission device when positioning the test specimen into the clamping device is prevented.

In one embodiment, the actuation device is a switch or a pressure control valve activatable via the actuation lever.

In one embodiment, the power gain element is at least one lever, preferably an L-shaped lever, pivotally connected to the frame.

In one embodiment, sealing means are arranged at the corresponding contact area of the upper clamping ring and of the lower clamping ring.

This allows preventing exit of water at a boundary area of the test specimen. Even when testing laminated textile exiting of water is prevented. Thus, untimely stop of testing can be prevented since the liquid container can not run out of water.

In one embodiment, the sealing means are O-rings or sealing rings with an X-shaped cross-section.

This allows clamping the test specimen firmly between the upper pressing ring and the lower pressing ring with the possibility to adapt the contact area of the sealing rings to the surface of the test specimen within a certain tolerance range. At the same time, a multistage sealing system can be provided.

In one embodiment, the sealing means of the upper clamping ring is a sealing member out of metal or ceramic or rigid resin.

Thereby, a waterproof sealing can be provided even for a test specimen made out of a material difficult to make sealed waterproof at its boundary area, i.e. in its contact area where the test specimen is clamped between the upper pressing ring and the lower pressing ring.

In one embodiment, the sealing member has two grooves each having a squared cross section and wherein, one of the grooves has a contact tip protruding to the outside of the groove. Alternatively, the sealing member has a plane underside.

Another aspect of the invention relates to a method for determining the resistance of a test specimen to liquid penetration in operating a hydrostatic head tester arrangement according to the present invention comprising at least the steps of:
  a) clamping the test specimen with a clamping device;
  b) activating a power transmission device only when the clamping device is in a predefined closed position;
  c) applying a test pressure onto one surface of the test specimen.

In one embodiment, the test pressure generating container is operationally connected to the power transmission device via an actuation device.

Figure 2A:
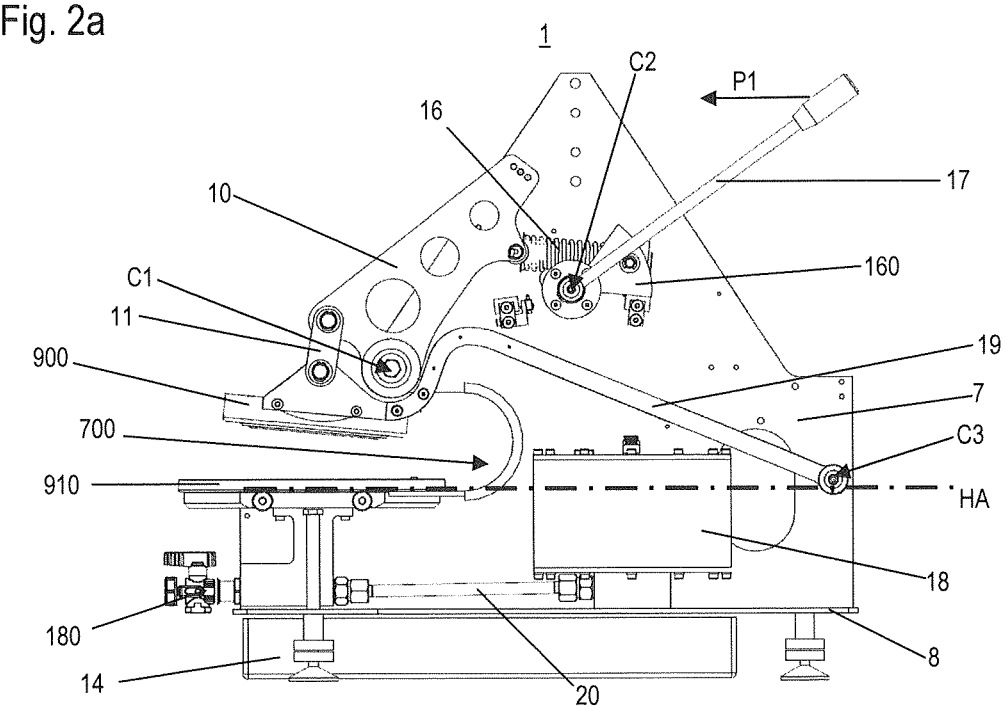
Figure 3B:
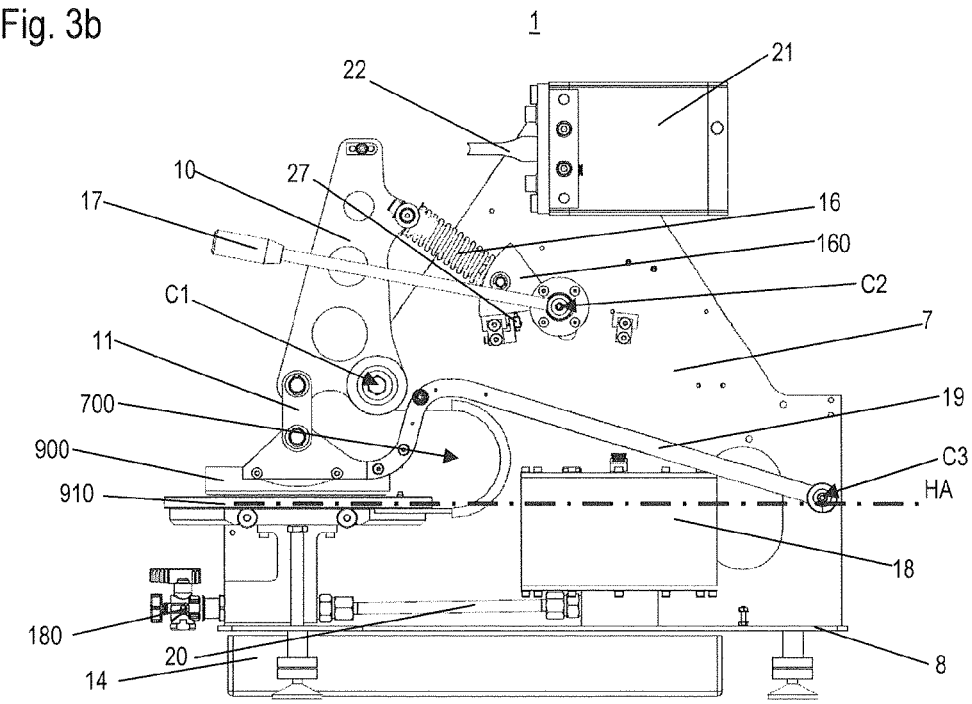
Figure 3C:
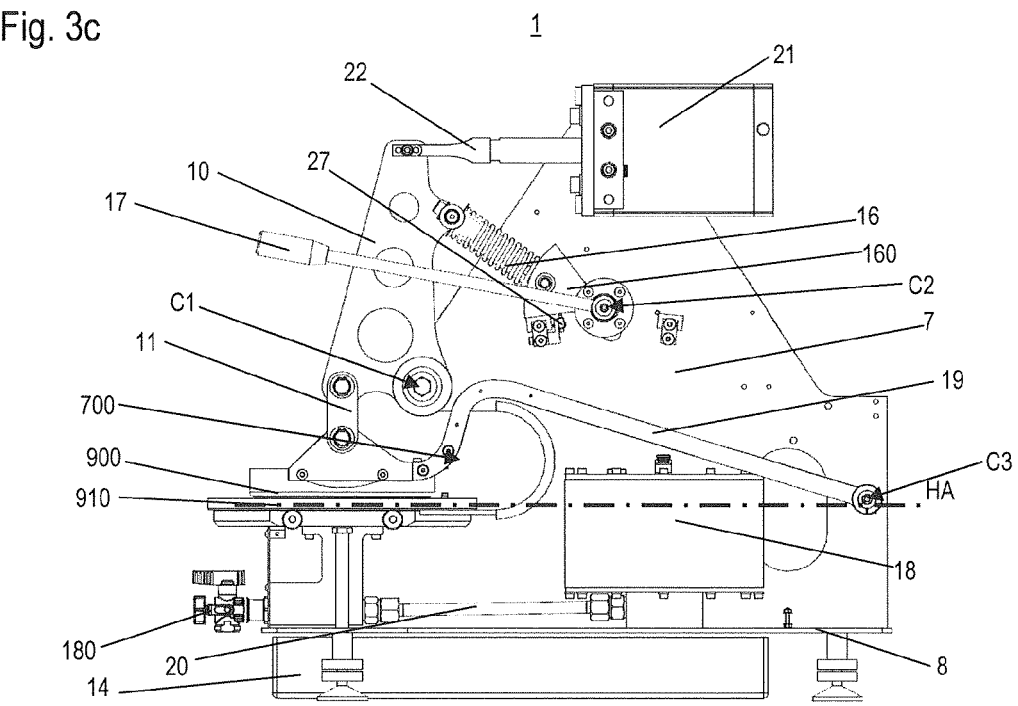

The present invention is further explained with the aid of exemplified embodiments, which are shown in figures. There is shown in:

FIG. 1, schematically, a perspective view of a hydrostatic head tester arrangement according to the present invention;

FIGS. 2a to 2b, schematically, a side view of a hydrostatic head tester arrangement in its inactivated state and in its activated state;

FIGS. 3a to 3c, schematically, a side view of a further hydrostatic head tester arrangement according to the present invention in its inactivated state and in its activated state; and FIGS. 4a to 4e, schematically, sealing means according hydrostatic head tester arrangements according to one of the FIGS. 1 to 3b.

In FIG. 1, schematically, a perspective view of a hydrostatic head tester arrangement 1 according to the present invention is depicted. The hydrostatic head tester arrangement 1 comprises a housing 2 wherein a display 3 is arranged in the upper front of the housing 2. An emergency switch 4, a printer device 5 for printing test results and a flash light 6 are arranged in a region of a top 200 of the housing 2. The top 200 and a side wall 210 of the housing 2 partly enclose a frame 7. The plate-like frame 7 is mounted onto a base plate 8. The frame 7 has a U-shaped recess 700. A clamping device 9 for clamping a test specimen (not shown in FIG. 1) comprises an upper clamping ring 900 and a lower clamping ring 910. The upper clamping ring 900 is connected to a power gain element 10 implemented as two parallel levers 10 each via a corresponding articulation member 11. A shaft 12 is arranged between the two levers 10. Alternatively, it is also conceivable to connect the upper clamping ring to one single lever via one single articulation member. A ring-shaped support 13 encloses the lower clamping ring 910. The ring-shaped support 13 serves to drain away test liquid, i.e. water for example, into an overflow container 14. A drain tap 180 is provided in the arrangement 1. An actuation lever 17 for clamping the upper clamping ring 900 ring against the lower clamping ring 910 is depicted in FIG. 1. Furthermore, the arrangement 1 comprises a main switch 15 in a region of the side wall 210 of the housing 2.

In FIG. 2a, schematically, a side view of a hydrostatic head tester arrangement 1 is depicted in its inactivated state. In its inactivated state, i.e. in a test preparation position, the upper clamping ring 900 is arranged remote from the lower clamping ring 910. The upper clamping ring 900 can be brought into a clamping position by activating manually the actuation lever 17. In the clamping position, a test specimen (not shown in FIG. 2a) is held by the clamping device 9. The power gain element 10 is connected to the actuation lever 17 via a resilient member 16. The resilient member 16 is a spring for example. The spring 16 is coupled or attached to a base part of the actuation lever 17 and to the power gain element 10 via a coupling element 160. It is also conceivable to implement the actuation lever 17 as an automatically driven lever member, wherein the automatically driven lever member is to be activated via a switch for example. Furthermore, each of the L-shaped levers 10 is pivotally connected to the frame 7 in a centre of rotation C1. Further, the actuation lever 17 is connected to the frame 7 in a second centre of rotation C2. The power gain element 10 i.e. the L-shaped lever, and the actuation lever 17 are connected to each other via the spring 16. The actuation lever 17 is manually operated in direction to the clamping device 9 depicted by an arrow P1. A test pressure generating device 18 implemented as a test pressure generating container with test liquid inside, i.e. water, is arranged in a region of the base plate 8. The drain tap 180 is operationally connected to the test pressure generating container 18 via a connecting tube 20. A guide arm 19 is attached in fix manner at one of its endings to the upper clamping ring 900. This ending is of a curved shape. The other ending is pivotally connected to the frame 7 at a third centre of rotation C3. The third centre of rotation C3 is arranged within the same horizontal axis HA as a horizontal surface of the stationary mounted lower clamping ring 910. The third centre of rotation C3 is located as far as possible away from the lower clamping ring 910. This allows positioning of the upper clamping ring 900 in substantially parallel manner with respect to the lower clamping ring 910.

In FIG. 2b, schematically, a side view of a hydrostatic head tester arrangement 1 is depicted in its activated state. In its activated state of the arrangement 1, the upper clamping ring 900 is clamped against the lower clamping ring 910. The test pressure generating container 18 transmits a test pressure onto the opposite surface of the test specimen.

In FIG. 3a, schematically, a side view of a further hydrostatic head tester arrangement 1 according to the present invention is depicted. The arrangement 1 of FIG. 3a differs to the arrangement 1 of FIG. 2 in that the actuation lever 17 and a power transmission device 21 form a two-stage activatable power transmission arrangement. The power transmission device 21 comprises a movable steering rod 22. In the inactivated state of the arrangement 1, the upper clamping ring 900 is distant from the lower clamping ring 910. Furthermore, the movable steering rod 22 is arranged distant from the power gain element 10, i.e. the L-shaped lever.

In FIGS. 3b to 3c, the arrangement 1 is depicted in its activated state. The activated state comprises at least two different types of activated states, namely a clamping position according to FIG. 3b and a testing position according to FIG. 3c. In both positions, the upper clamping ring 900 is clamped against the lower clamping ring 910. The clamping position (see FIG. 3b) differs from the testing position (see FIG. 3c) in that the test specimen is held by the clamping device 9 without being exposed to a predetermined contact pressure, wherein the predetermined contact pressure is considerably greater than the contact pressure for merely holding the test specimen in its position. Only when the clamping device 9 is in its designated correct closed position, the predetermined contact pressure can be exerted on the upper pressing ring 900 in engaging a free ending of the movable steering rod 22 to the power gain element 10. This can be implemented e.g. in activating an actuation device 27 for activating the power transmission device 21. The actuation device 27 can be a switch or a pressure control valve coupled to the power transmission device 21.

In a test preparation position, which corresponds to the inactivated state of the arrangement 1 as depicted in FIG. 3a, the test specimen is placed onto the lower clamping ring 910. The arrangement 1 is brought into its clamping position in clamping the upper clamping ring 900 against the lower pressing ring 910 (see FIG. 3b). Thereby, the clamping device 9 is brought into a closed position and the test specimen is held by the clamping device 9. After that, the predetermined contact pressure can be exerted on the upper clamping ring 900 in activating the power transmission device 21. The actuation device 27 connected or coupled to the power transmission device 21 is only activated when the clamping device 9 is closed i.e. the upper clamping ring 900 is clamped against the lower clamping ring 910. Thereby, accidents like bruising of fingers of the user can be prevented. The actuation device 27 can be implemented e.g. as a switch or a pressure control valve. When the clamping device 9 is in its correct closed position, the predetermined contact pressure is applied on the upper clamping ring 900. Subsequently or at the same time, a test pressure can be applied on the opposite surface of the test specimen for determining the resistance of the test specimen to liquid penetration.

In FIGS. 4a to 4e, schematically, sealing means 23 of the upper clamping ring 900 and of the lower clamping ring 910 according to one of the hydrostatic head tester arrangements 1 according to one of the FIGS. 1 to 3b are depicted.

Figure 4A:
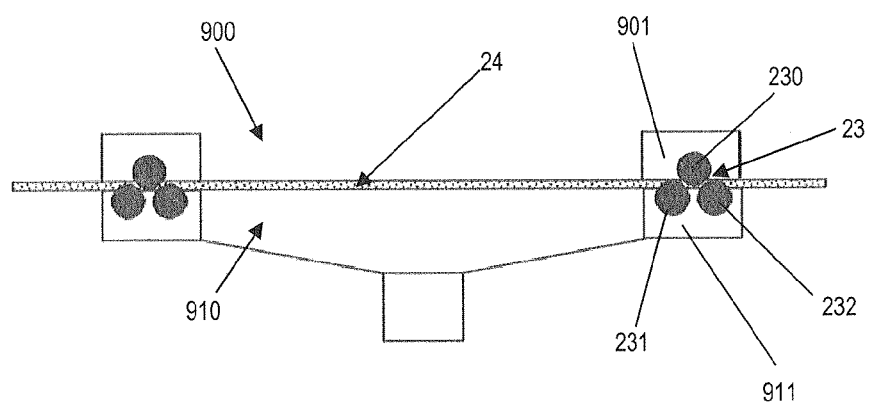

In FIG. 4a, a contact area 901 of the upper clamping ring 900 is clamped against a further contact area 911 of the lower clamping ring 910. Each of the contact areas 900, 910 comprises sealing means 23 in form of O-rings 230, 231, 232. The sealing means 23 are arranged in a region of the outer edge of the disk like upper and lower clamping rings 900, 910. In FIG. 4a, one 230 of the O-rings 230, 231, 232 are arranged at the outer edge of the upper pressing ring 900.

The other two O-rings 231, 232 of the O-rings 230, 231, 232 are arranged at the outer edge of the lower clamping ring 910. The O-ring 230 of the upper clamping ring 900 is arranged between the two O-rings 231, 232 of the lower clamping ring 910. Thereby, a waterproof contact area is formed between the upper clamping ring 900 and the lower clamping ring 910 in order to seal a test specimen 24 in waterproof manner against leakage of water in the region of the waterproof contact area. In the testing position of the hydrostatic head tester arrangement 1, the test specimen 24 is clamped between the upper clamping ring 900 and the lower clamping ring 910. Thus, the sealing means 23 of FIG. 4a ensure a two-point sealing function.

Figure 4B:
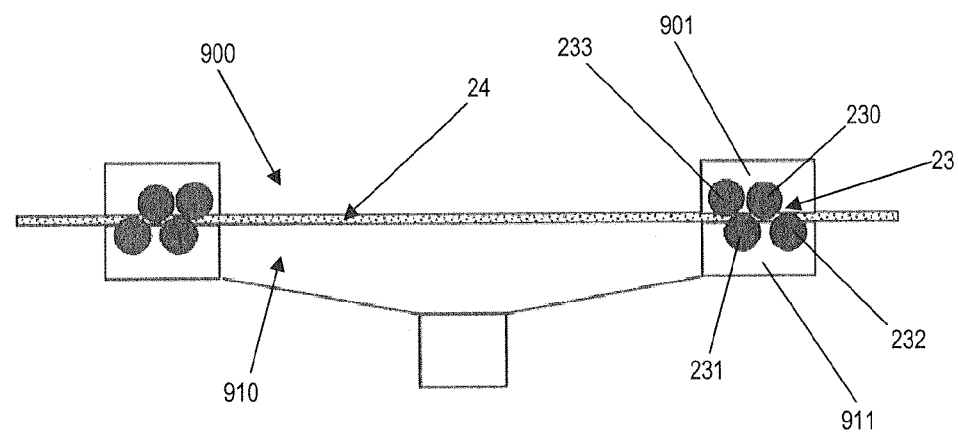

FIG. 4b differs to FIG. 4a in that the contact area 900 of the upper clamping ring 900 comprises two O-rings 230, 233. Therewith, a multilevel sealing system can be provided.

Figure 4C:
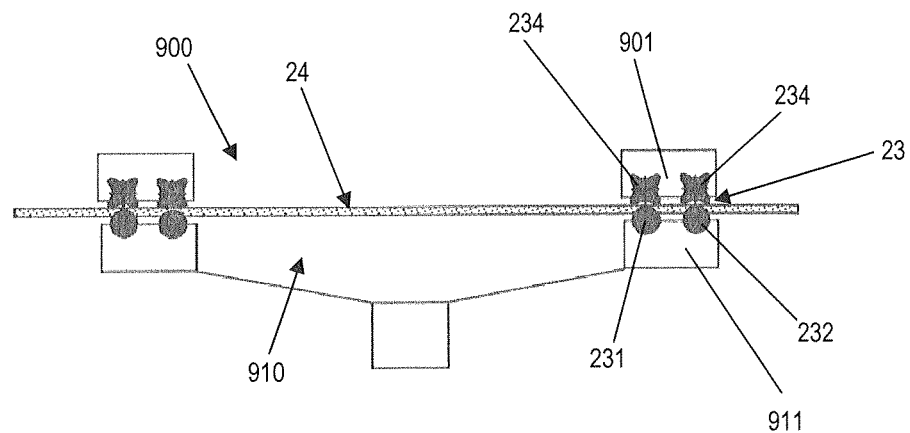

FIG. 4c differs to the FIGS. 4a to 4b in that the sealing means 23 of the upper clamping ring 900 are sealing rings 234 of an X-shaped cross section.

Figure 4D:
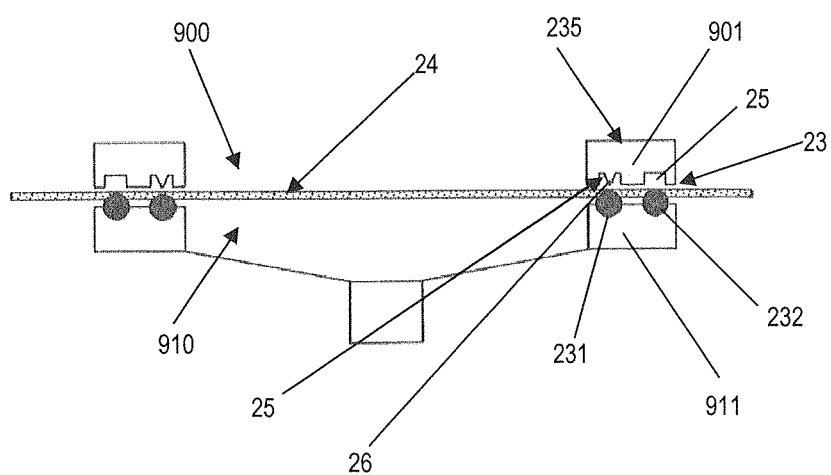

FIG. 4d differs to the FIGS. 4a to 4c in that the sealing means 23 of the upper clamping ring 900 are sealing members 235 out of metal or ceramic or rigid resin. Each of the sealing members 235 has at least one groove 25. One of the grooves 25 further has a contact tip 26 protruding to the outside of the groove 25.

Figure 4E:
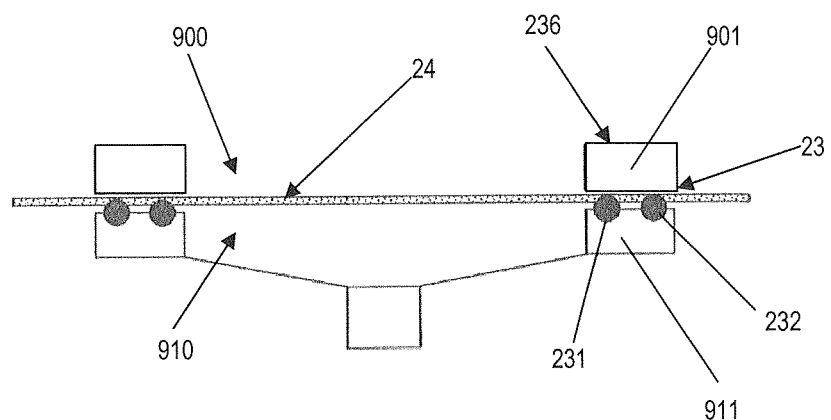

FIG. 4e differs to FIG. 4d in that the sealing means 23 of the upper clamping ring 900 are sealing members 236 having a plane contact surface or a plane underside.

The invention claimed is:

1. Hydrostatic head tester arrangement comprising:
a frame;
a test pressure generating device;
a clamping device having first clamping ring and a second clamping ring;
a power gain element connected to the first clamping ring, characterized in that the power gain element is connected to an actuation lever via a resilient member; and
a power transmission device comprising a movable steering rod, its operating free end arranged distant from the power gain element in its inactivated state and engaging the power gain element in its activated state.

2. Hydrostatic head tester arrangement according to claim 1, characterized in that the first clamping ring is an upper clamping ring and the second clamping ring is a lower clamping ring, wherein a guide arm is attached to the upper clamping ring and is pivotally connected to the frame and the power gain element is connected to the upper clamping ring or to the guide arm via an articulation member.

3. Hydrostatic head tester arrangement according to claim 1, characterized in that the power transmission device comprises a pneumatic pressure cylinder or a hydraulic pressure cylinder or an electric driven pressure spindle.

4. Hydrostatic head tester arrangement according to claim 1, characterized in that the power transmission device is coupled electrically or pneumatically or hydraulically to an actuation device to be activated.

5. Hydrostatic head tester arrangement according to claim 4, characterized in that the actuation device is a switch or a pressure control valve activatable via the actuation lever.

6. Hydrostatic head tester arrangement according to claim 1, characterized in that the power gain element is at least one lever, preferably an L-shaped lever, pivotally connected to the frame.

7. Hydrostatic head tester arrangement according to claim 1, characterized in that sealing means are arranged at the corresponding contact area of the upper clamping ring and of the lower clamping ring.

8. Hydrostatic head tester arrangement according to claim 7, characterized in that the sealing means are O-rings or sealing rings with an X-shaped cross-section.

9. Hydrostatic head tester arrangement according to claim 7, characterized in that the sealing means of the upper clamping ring is a sealing member out of metal or ceramic or rigid resin.

10. Hydrostatic head tester arrangement according to claim 9, characterized in that the sealing member has two grooves each having a squared cross section and wherein one of the grooves has a contact tip protruding to the outside of the groove or wherein the sealing member has a plane underside.

11. Method for determining the resistance of a test specimen to liquid penetration in operating a hydrostatic head tester arrangement according to claim 1 comprising at least the steps of:
a) clamping the test specimen with a clamping device (9);
b) activating a power transmission device only when the clamping device is in a predefined closed position;
c) applying a test pressure onto one surface of the test specimen.

12. Method according to claim 11, wherein a test pressure generating container is operationally connected to the power transmission device via an actuation device.

* * * * *